US006991611B2

(12) United States Patent
Rhee

(10) Patent No.: US 6,991,611 B2
(45) Date of Patent: Jan. 31, 2006

(54) POSTURE APPARATUS

(76) Inventor: Jhoon Goo Rhee, 4068 Rosamora Ct., McLean, VA (US) 22101

( * ) Notice: Subject to any disclaimer, the term of this patent is extended or adjusted under 35 U.S.C. 154(b) by 131 days.

(21) Appl. No.: 10/366,565

(22) Filed: Feb. 14, 2003

(65) Prior Publication Data

US 2003/0153855 A1   Aug. 14, 2003

Related U.S. Application Data

(60) Provisional application No. 60/356,115, filed on Feb. 14, 2002.

(51) Int. Cl.
*A61F 5/00* (2006.01)
(52) U.S. Cl. .............................. 602/4; 602/19; 128/869
(58) Field of Classification Search .................. 602/4, 602/5, 19; 128/869, 876; 450/1, 17, 18, 450/23, 25
See application file for complete search history.

(56) References Cited

U.S. PATENT DOCUMENTS

| 3,141,456 | A |   | 7/1964  | Meek |
| 3,277,889 | A |   | 10/1966 | Palmer |
| 3,338,236 | A |   | 8/1967  | McLeod, Jr. |
| 3,382,868 | A |   | 5/1968  | Stiefel |
| 3,856,004 | A |   | 12/1974 | Cox |
| 3,897,776 | A |   | 8/1975  | Gaylord, Jr. |
| 4,031,900 | A | * | 6/1977  | Guidoni ..................... 450/69 |
| 4,076,029 | A | * | 2/1978  | Wiquel ........................ 450/1 |
| 4,785,803 | A |   | 11/1988 | Benckhuijsen |
| 5,018,513 | A |   | 5/1991  | Charles |
| 5,067,484 | A |   | 11/1991 | Hiemstra-Paez |
| 5,116,306 | A |   | 5/1992  | Zander |
| 5,120,288 | A |   | 6/1992  | Sinaki |
| 5,135,470 | A |   | 8/1992  | Reeves |
| 5,360,391 | A |   | 11/1994 | Johnson |
| 5,405,313 | A |   | 4/1995  | Albin |
| 6,319,091 | B1 | * | 11/2001 | Kilbride et al. .............. 450/17 |

* cited by examiner

*Primary Examiner*—Michael Anthony Brown
(74) *Attorney, Agent, or Firm*—McGuireWoods LLP

(57) ABSTRACT

A posture system is made from a single strap and having opposing ends. At the opposing ends are fastening elements. In use, the user places the strap about the back of the user's neck "N" and, thereafter, crosses the strap 100 at a point on the user's back. During tension, the user fastens the strap in order to secure the strap to the user. The loops across the front of the shoulders pull the shoulders back or remind a user to pull the shoulders back for better posture and health.

15 Claims, 13 Drawing Sheets

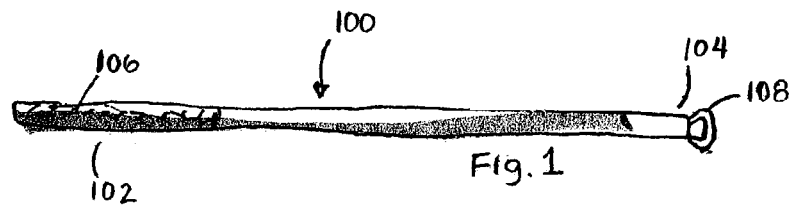
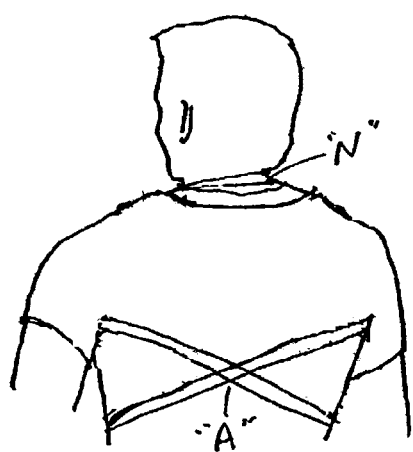
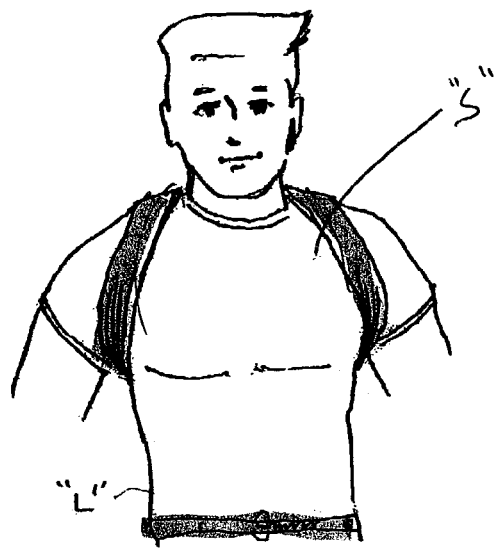
Fig. 1
Fig. 2
Fig. 3
Fig. 4

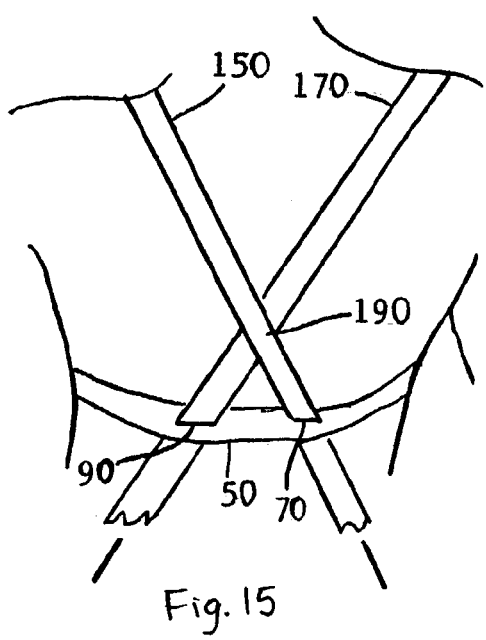
Fig. 15
FIG. 16
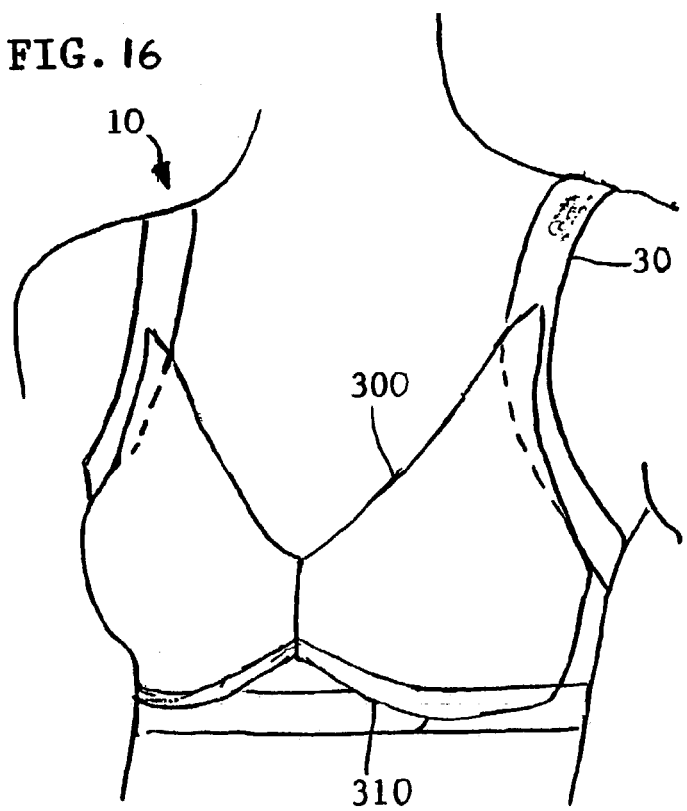

POSTURE APPARATUS

This application claims the benefit of U.S. Provisional Patent Application No. 60/356,115 filed on Feb. 14, 2002, which is hereby incorporated by reference for all purposes as if fully set forth herein.

BACKGROUND OF THE INVENTION

1. Field of the Invention

The present invention generally relates to a posture apparatus and, more particularly, to a strap used to improve a user's posture by maintaining shoulders in a rearward position thereby discouraging a forward rounding of the shoulders.

2. Discussion of the Related Art

Proper posture is perhaps the most singular signal of good health, well being, self confidence and good body condition. Good posture, and particularly holding the shoulders back, besides providing good appearance, in of itself creates good health. Holding the shoulders back provides natural enlargement of space in which body organs operate. Lungs can expand more readily, moving greater quantities of air and thus reducing respiration rate. External pressure on the heart is reduced, thus creating a possibility for greater pumping volumes and the potentiality for reducing heart rate, and particularly resting heart rate.

Proper posture can also reduce blood pressure. External pressure on organs, such as the stomach, liver, intestines, kidneys, bladder, pancreas and others may be reduced, and their activities may be improved by pulling the shoulders backward and thus increasing the volume of the cavities in which those organs operate.

Pulling the shoulders backwards produces figure improvement for women and may reduce the desirability or need for lifting, pushing or augmenting soft tissue for figure enhancement.

The related art systems to improve posture systems generally are complex. For example, the related art systems include complex braces and splints making their ordinary use cumbersome and difficult. Additionally, putting on the braces is difficult, and adjusting them may require several steps. Moreover, cleaning the complex devices increases the difficulty of their use and may also discourage the use of the apparatuses.

By way of example, U.S. Pat. No. 3,338,236 by McLeod Jr. shows a related art system. Disclosing a clavicle splint that includes at least three different components, a central strap, felt and stocking net. These components make the splint difficult to clean, as well as cumbersome and difficult to wear. Also, the device fits only about the shoulders and does not have any component for easy adjustments, and the like.

U.S. Pat. No. 5,067,484 by Miemstra-Paez shows a posture training device. In this device, there are two straps adapted to loop around a shoulder of a user and a centrally located rear pouch. The rear pouch is designed to hold weights. Each of the loops are individually adjusted. However, much like the device shown in U.S. Pat. No. 3,338,236 the device only fits around a user's shoulders. (See, also U.S. Pat. No. 5,120,288 to Sinaki and U.S. Pat. No. 5,116,306 to Zander).

An additional related art system is described in U.S. Pat. No. 3,897,776 by Gaylord, Jr. This device includes a strap adapted to interconnect with a rear centrally located buckle system. In order to operate this device, the user must arrange the strap to the buckle system at the back of the user. This may be very difficult, if not impossible, for some users to wear.

Accordingly, there is a need for an inexpensive and simple posture system and, more particularly, for a posture system that is not complex and simple to use. The present invention obviates one or more of the problems associated with related art.

SUMMARY OF THE INVENTION

Accordingly, the present invention is directed to posture system that substantially obviates one or more of the problems due to limitations and disadvantages of the related art.

An advantage of the present invention is to provide a simple inexpensive posture improving device.

Another advantage of the present invention is to provide a posture improving device that can be used with undergarments.

Yet another advantage of the present invention is to provide a posture system that is not complex and simple to use.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, discloses a posture apparatus, including a fabric strap having central longitudinal slits and ends half twisted inwardly and crossed. The fabric strips are passed through the slits, forming back and shoulder loops for inserting arms of a user. Opposite ends of the straps may include complementary fasteners for connecting the opposite ends after tightening the strap. Tightening the strap tends to pull back shoulders of a user and straighten a user's posture.

In another aspect of the present invention, a posture apparatus, may include a single fabric strap having a first end and a second end. The strap is twisted, thereby forming shoulder loops. Fasteners are arranged on the first end and the second end of the straps for engaging and holding the ends after pulling on the ends and tightening the loops.

In yet another aspect of the present invention, a method for improving posture, includes arranging a first end and a second end of an elongated strap around a user's neck and under the user's arm pits and crossed around the user's back. The arrangement of the strap, thereby forming loops around the arms and shoulders of a user. Next, pulling on the first and second ends of the strap, thereby tightening the loops and pulling shoulders of the user rearward. While continuing to pull the ends of the loops, fastening the ends of the loops in front of the user, thereby holding the loops in their tightened position while urging a user's shoulders backward. Accordingly, the user posture may be improved.

It is to be understood that both the foregoing general description and the following detailed description are exemplary and explanatory and are intended to provide further explanation of the invention as claimed.

BRIEF DESCRIPTION OF THE DRAWING

The accompanying drawings, which are included to provide a further understanding of the invention and are incorporated in and constitute a part of this specification, illustrate embodiments of the invention and together with the description serve to explain the principles of the invention.

In the drawings:

FIG. 1 illustrates a perspective view of the posture system according to an embodiment of the present invention;

FIG. 2 illustrates a rear view of a user with the posture system according to an embodiment of the present invention strapped around the shoulders and back;

FIG. 3 illustrates a front view of a user with the posture system according to an embodiment of the present invention strapped around the shoulders and waist;

FIG. 4 illustrates a top view of a user during and after use according to an embodiment of the present invention;

FIG. 15 illustrates the back of the posture system shown in FIG. 6.

FIG. 16 illustrates the posture system according to another embodiment of the present invention to which a brassiere top attachment has been added;

DETAILED DESCRIPTION OF THE ILLUSTRATED EMBODIMENTS

Figure 5:
FIG. 5 illustrates a side view of a user during and after use according to an embodiment of the present invention.

Reference will now be made in detail to various embodiments of the present invention, examples of which is illustrated in the accompanying drawings.

FIG. 1 illustrates a perspective view of the posture system according to an embodiment of the present invention Referring to FIG. 1, the posture system is generally depicted as reference numeral 100 and includes a single strap having a first end 102 and a second end 104. Fastening mechanisms are provided at the respective first 102 and second 104 ends of the strap 100. More particularly, the first end 102 may include a velco® strip 106 and the second end 104 may include a buckle 108 for fastening the first and second ends together. By using this fastening mechanism, as well as others described below, the strap of the present invention is adjustable about the user's shoulders and waist.

It should be well understood by those of ordinary skill in the art that the strap 100 may be made from or include any durable, strong material and is beneficially made of a soft, thin material that is comfortable on the skin. Also, the fastening mechanisms 106 and 108 may be other types of mechanisms such as, for example, snap buckles, zippers, buttons, micro loop and hook fastener strips and the like. However, these fastening mechanisms should not be deemed a limiting factor and are provided for illustrative purposes. The ends may also be fastened to a belt. Also, at least one end of the strap 100 may be adjustable (i.e., severable in sections from the remainder of the strap) for shortening or lengthening the strap 100.

FIG. 2 illustrates a rear view of a user with the posture system according to an embodiment of the present invention strapped around the shoulders and back. FIG. 3 illustrates a front view of a user with the posture system according to an embodiment of the present invention strapped around the shoulders and waist.

Referring to FIGS. 2 and 3, the strap 100 may be placed about the back of the user's neck "N", and then in front of the shoulders "S" as shown, for example, in FIG. 3. Thereby, the strap forms respective loops around the shoulders. Thereafter, the strap 100 may be crossed at substantially point "A" on the user's back as shown in FIG. 2. Next, the strap 100 is tightened and fixed about the user's waist, preferably below the belt line "L" as shown in FIG. 3. In this manner, the posture system of the present invention is capable of improving a user's posture by maintaining shoulders in a rearward position, thereby discouraging a forward rounding of the shoulders.

FIGS. 4 and 5 illustrate improvement of the user's posture by using the posture apparatus according to an embodiment of the present invention.

FIG. 4 illustrates a top view of a user before, during and after use of the present invention. FIG. 5 illustrates a side view of a user before, during and after use of the present invention. In both of these figures, the solid lines represent a user's posture prior to the use of the present invention. The dashed lines, on the other hand, show that the user's shoulders are maintained in a rearward position during and after use of the present invention. The latter is illustrative of the user's improved posture.

The apparatus may be used with undergarments, such as brassieres as explained in greater detail below. Additionally, the apparatus ends 102 and 108 may be directly connected to other articles of clothing or undergarments as explained in greater detail, for example, with reference to FIG. 23.

Figure 6:
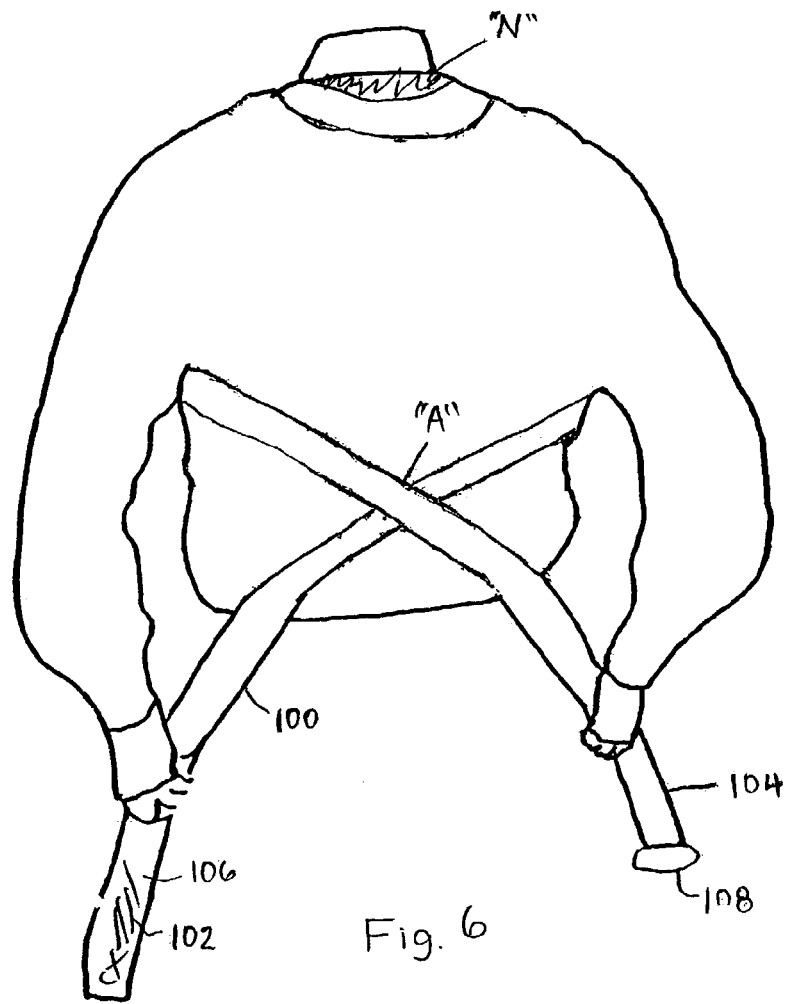
FIGS. 6 to 8 illustrate a method of using the posture system according to an embodiment.
Figure 7:
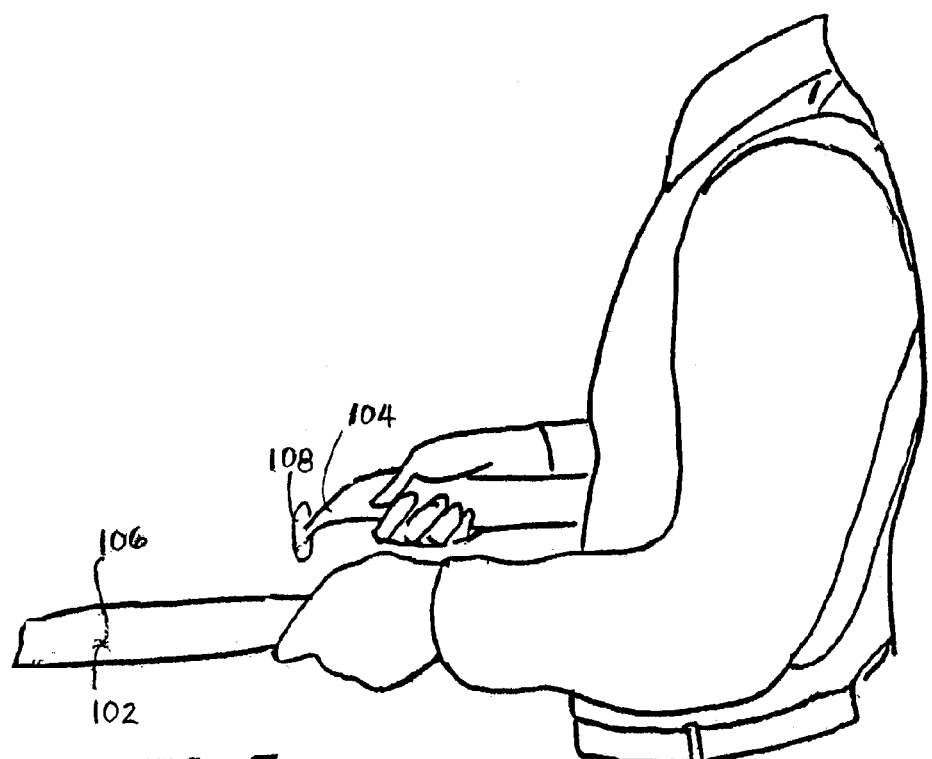
Figure 8:
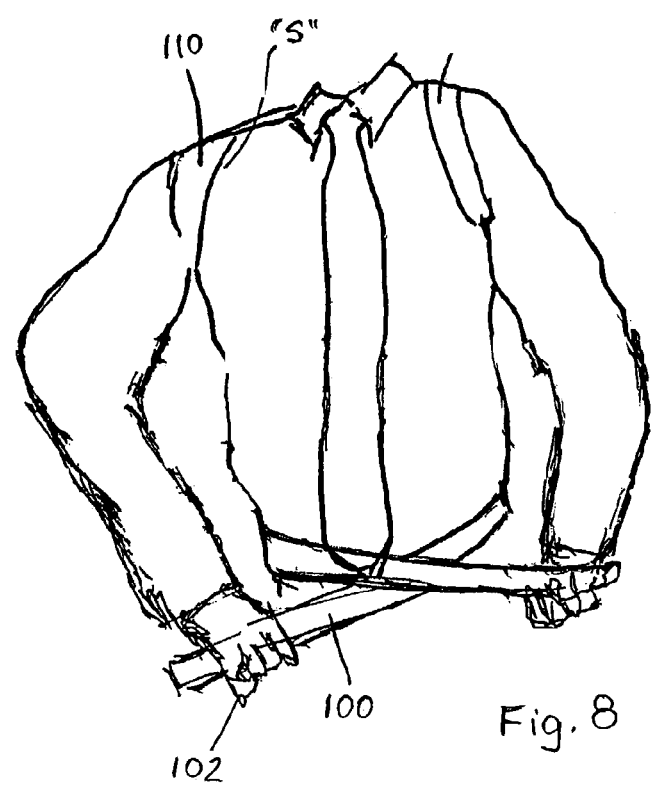

FIGS. 6 through 8 illustrate a method of arranging the posture system on a user according to an embodiment of the present invention.

Referring to FIG. 6, illustrating a user arranging the strap 100 around the back of the user's neck "N" and, thereafter, crossing the strap 100 at substantially point "A" on their back. In FIGS. 7 and 8, the user tightens the strap about their waist, preferably below the belt line "L". FIG. 8 also represents the user fasteneing the strap 100 in order to secure the strap 100 to their body. That is, while tensioned the ends 102 and 104 are fastened with the fastening mechanisms 106 and 108 (e.g., micro hook and loop fabric fasteners). As described above, the fastening mechanism may be any suitable fastening device.

While arranged on the user the loops across the front of the shoulders pull the shoulders back or remind a user to pull the shoulders back for better posture and health. Accordingly, the posture system of the present invention is capable of improving a user's posture by maintaining shoulders in a rearward position.

Figure 9:
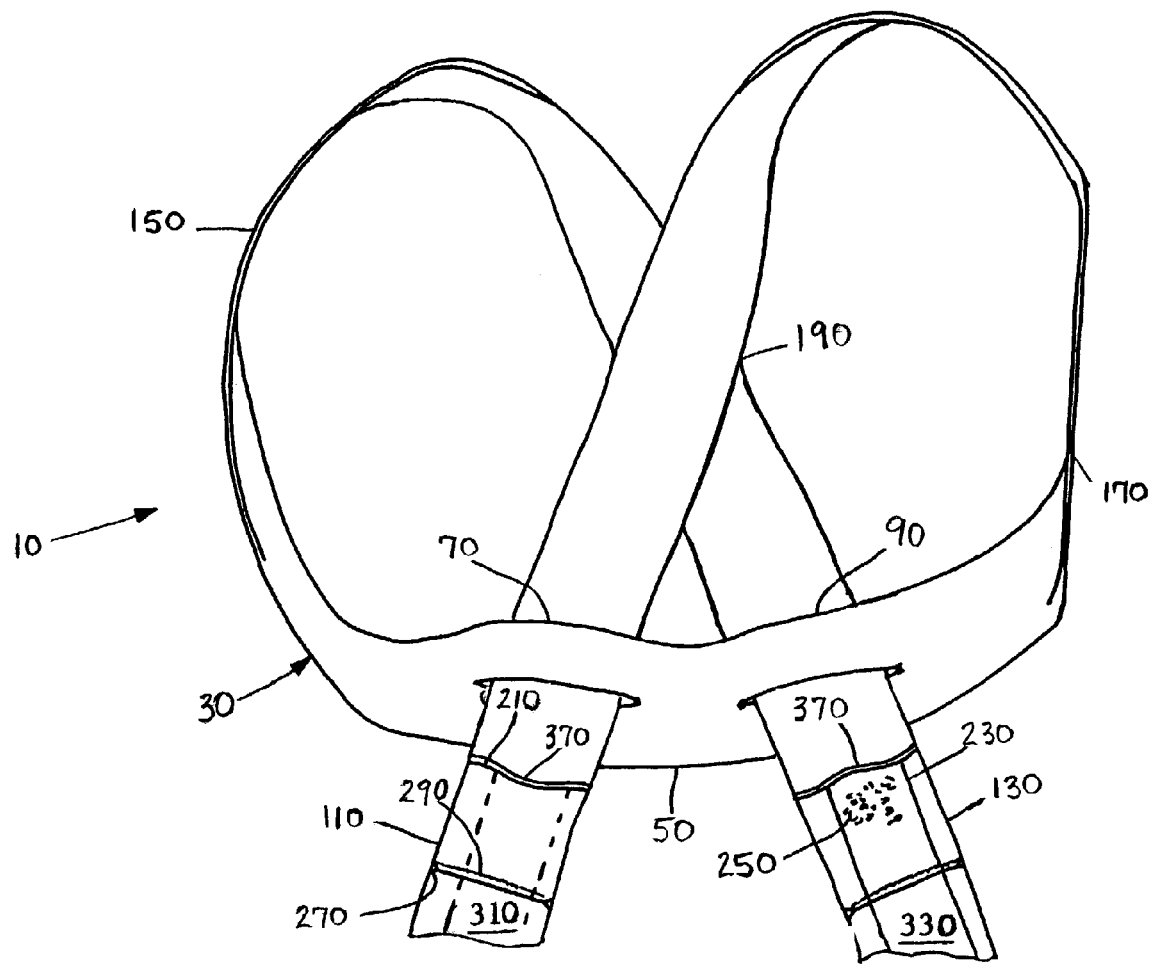
FIG. 9 illustrates perspective view of a posture system according to another embodiment of the present invention.

Additionally, variations have been contemplated, for example, FIG. 9 illustrates perspective view of a posture system according to a second embodiment of the present invention.

Referring to FIG. 9, the posture apparatus is generally indicated by the numeral 10 including a strap 30, which has a central portion 50 with receivers 70 and 90 for receiving end portions 110 and 130 of the strap 30. The receivers 70 and 90, as shown may be longitudinal slits formed in the longitudinal center of the strap 30. The slits may be positioned centrally or near an upper edge or near a lower edge of the strap, or the slits may be replaced with loops such as a cord or fabric strip sewn at ends to one face of the strap for receiving the ends 11 and 13 as they pass between the outside of the strap and the unsewn portion of the cord.

Passing the ends 110 and 130 through the receivers 70 and 90 forms loops 150 and 170, which are crossed at 190, which will be in a vertical center of a back of a user.

Before the ends 110 and 130 are placed through the receivers 70 and 90, the ends of the strap are twisted one half of a rotation so that the strap loops lie flat against the back and shoulders of a user.

Referring to FIG. 9, the end 110 has an elongated outward facing strip 210 of micro loops for cooperating with a complementary fastener on end 130. The complementary fastener on end 130 is an inward facing elongated strip 230 of micro hook fabric fasteners 250, which tightly engage and hold the micro loops of outward facing strip 210 on end 110.

Optionally, the entire surface of strap 30 or the entire outer surface of end 110 may be formed with a looped-type fabric in which the micro hooks 250 automatically engage upon juxtaposing, to firmly hold the ends.

The ends 110 and 130, or at least one of the ends, has notches 270 and stitches 290 sewn between the notches so that a distal end portion 310 or 330 may be severed from the remainder of the strap by cutting the strap between the notches. The actual notches 270 are not necessary, but are useful primarily in aligning scissors when making a cut. The notches 270 may be replaced by threads stitched across the strap ends as a guide for severing, or by printed lines or other indicia.

The ends 110 and 130 of the strap are shown foreshortened along lines 370 for convenience of illustration.

Figure 10:
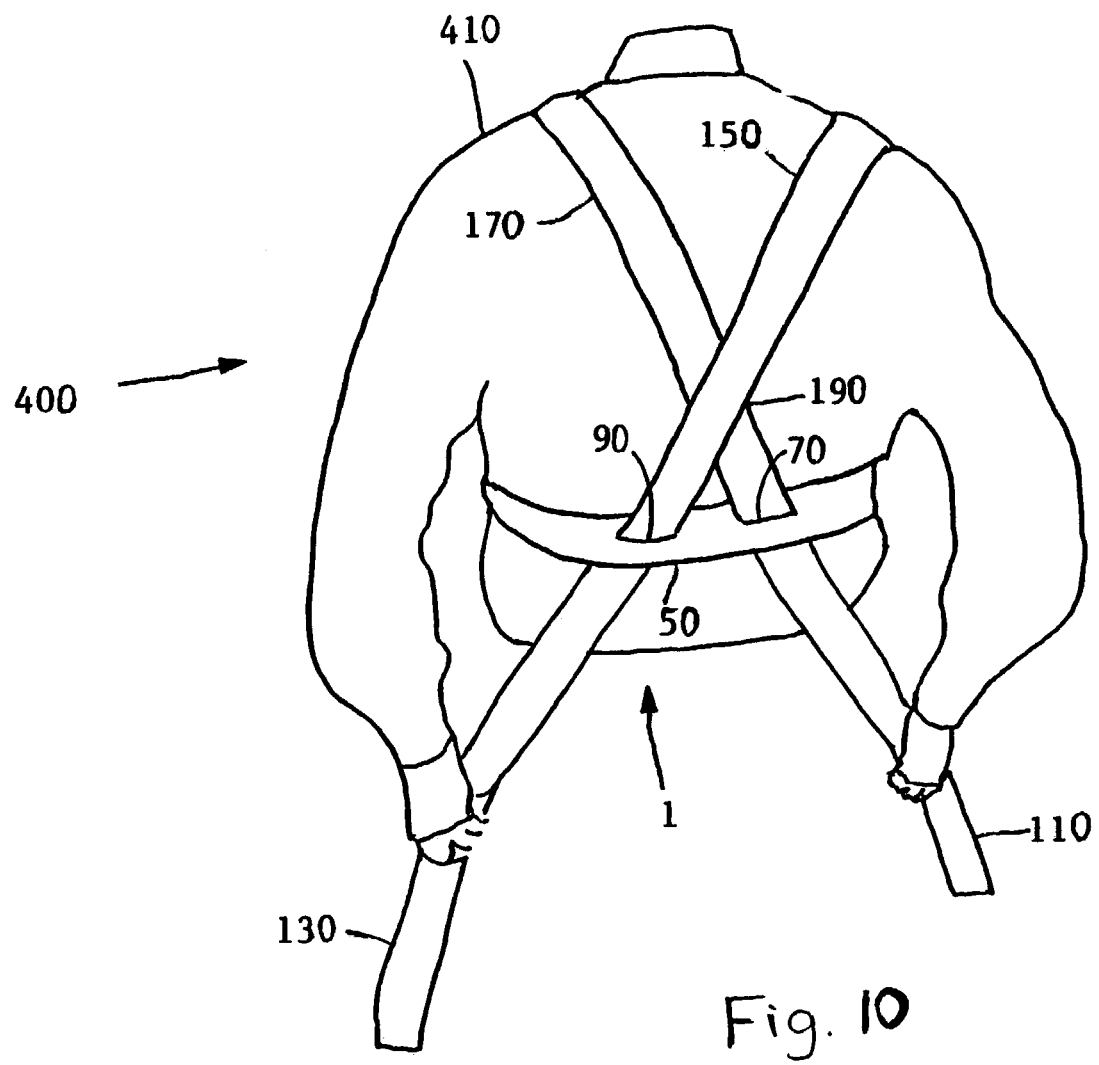
FIG. 10 illustrates a back view of the posture system according to another embodiment of the present invention.
Figure 11:
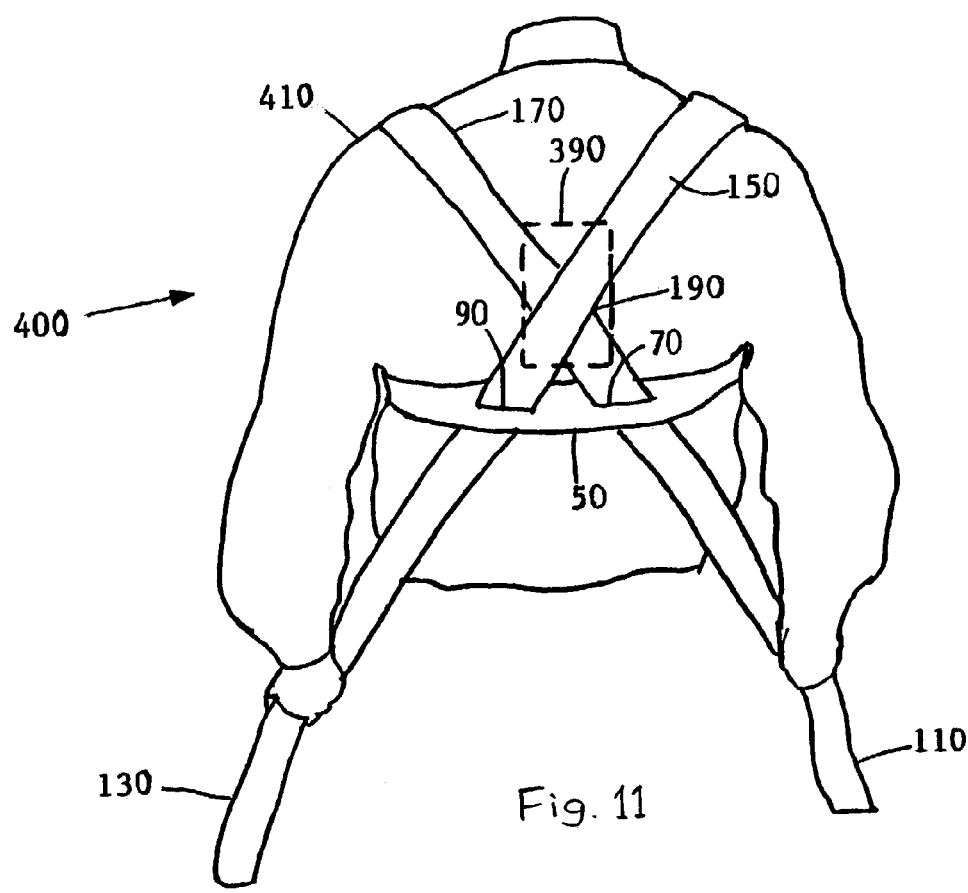
FIG. 11 illustrates a back view and operation of the posture system according to another embodiment of the present invention.
Figure 12:
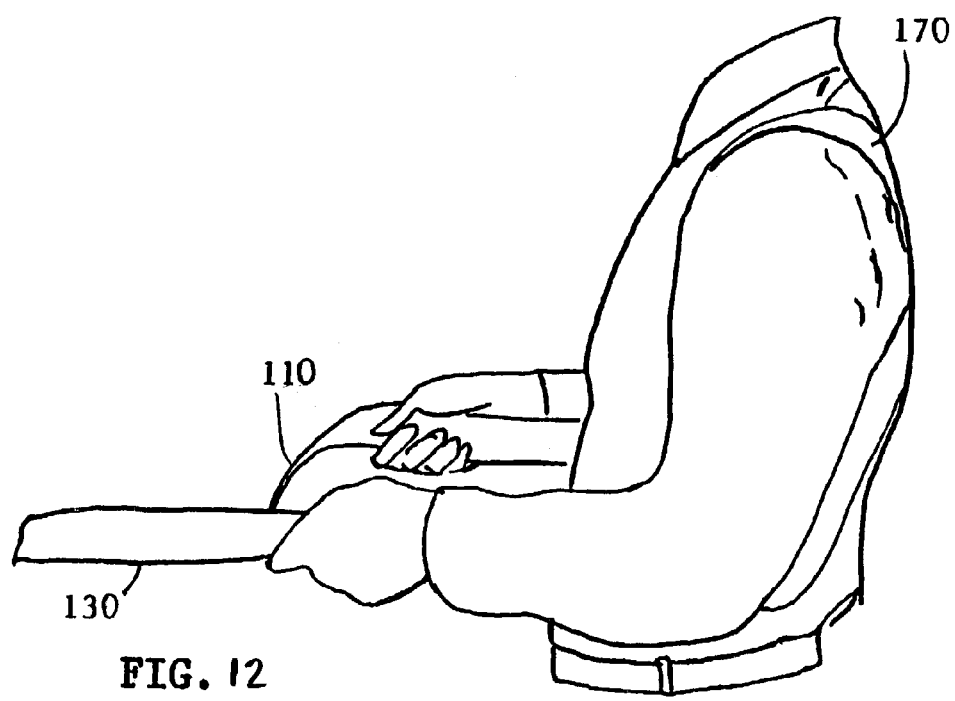
FIG. 12. illustrates a side view and operation of the posture system according to another embodiment of the present invention.
Figure 13:
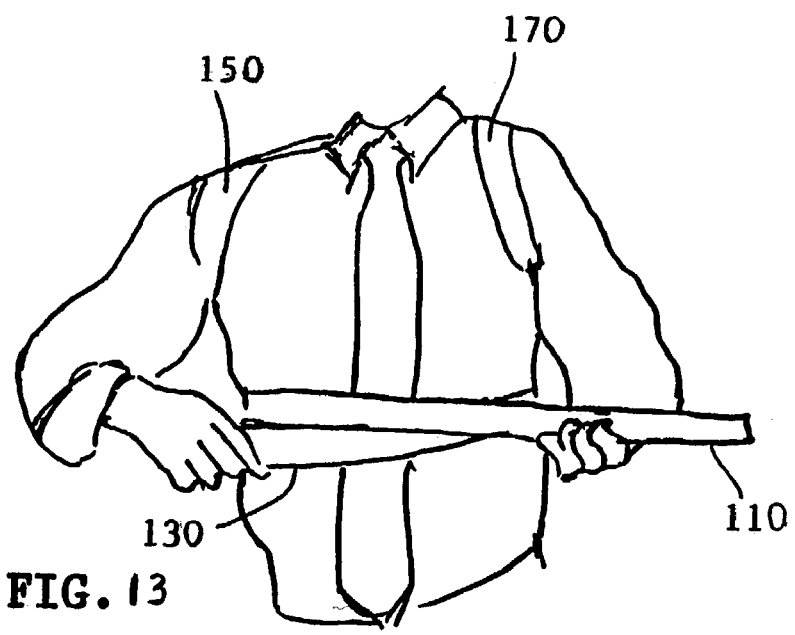
FIG. 13 illustrates operation of the posture system according to another embodiment of the present invention by pulling the ends of the straps across the front of the body prior to fastening the ends of the straps together.

Referring to FIG. 10, the loops 150 and 170 are arranged over the shoulders 410 of a user 400. The ends 110 and 130 are pulled downwardly and outwardly, thereby tightening the loops 150 and 170, which also slightly raises the central portion 50, as shown in FIG. 11. Next, while maintaining the tension on the strap ends 110 and 130, the strap ends are pulled to the forward position, as shown in FIG. 12. Finally, maintaining the tension, the straps are crossed, as shown in FIG. 13, and the straps are pressed together to fasten the apparatus.

Referring to FIG. 11, a box-like rigid pad or wallet 390 may be inserted under the crossed portion 190 of the loops 150 and 170 to aid in straightening the back and pulling the shoulders rearward or serving as a reminder to the user. The box-like pad or wallet 390 may be inserted after the ends are secured by sliding the pad 390 inside the cross 190. Optionally, the pad 390 may be provided with an adhered patch of micro loops to secure the pad to the innermost loop 170 before or after the apparatus is put on.

Figure 14:
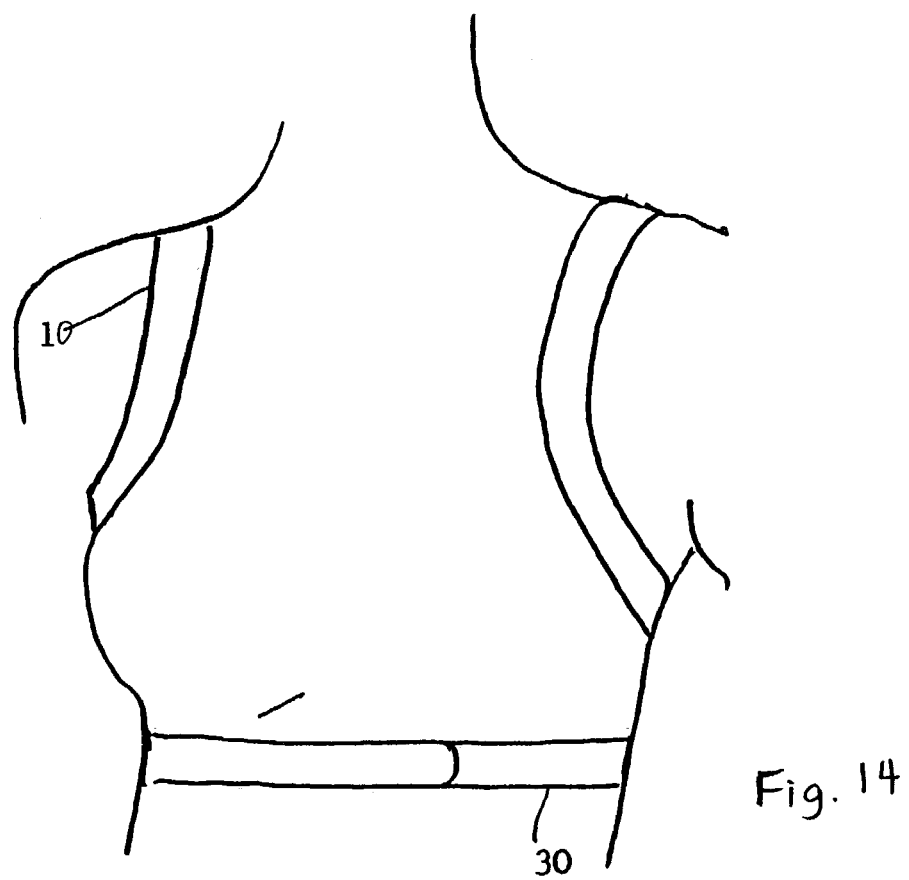
FIG. 14 illustrates the posture system according to another embodiment of the present invention being worn by a woman holding her shoulders back and improving posture and her figure.

Referring to FIG. 14, a woman may wear the posture system 10 with or without other upper body undergarments to improve the posture by holding the shoulders back, and at the same time to raise, shape and increase the apparent fullness of the chest. The strap 30 may be made of a thin lightweight satin material. Additionally, the strap may be made of any suitable material as described above.

The strap crosses the chest beneath the breast and is fastened in the front with any fastener, such as micro hook and loop fasteners, hooks and sewn loops, a small D-ring or any other form of attachment. Attaching the strap across the chest near the bottom of the sternum reminds a wearer to breathe deeply using a diaphragm for full expansion of the lungs.

The straps form loops 150 and 170 over the shoulders, which are slid through the receivers 70 and 90 in the central portion 50 of the strap, are pulled downward, as indicated by the arrows, and then are pulled forward and fastened in front of the user's sternum.

FIG. 8 shows another embodiment of the invention in which a breast cup attachment 300 is attached to the strap 30 of the posture apparatus 10. The breast cup attachment may have underwires, such as U-shape underwires 310 along lower edges. The breast attachment may be connected with hooks and loops to the strap 30. Alternatively, inward facing micro hook patches grip a soft outer pile surface on frontal portions of the strap.

Figure 17:
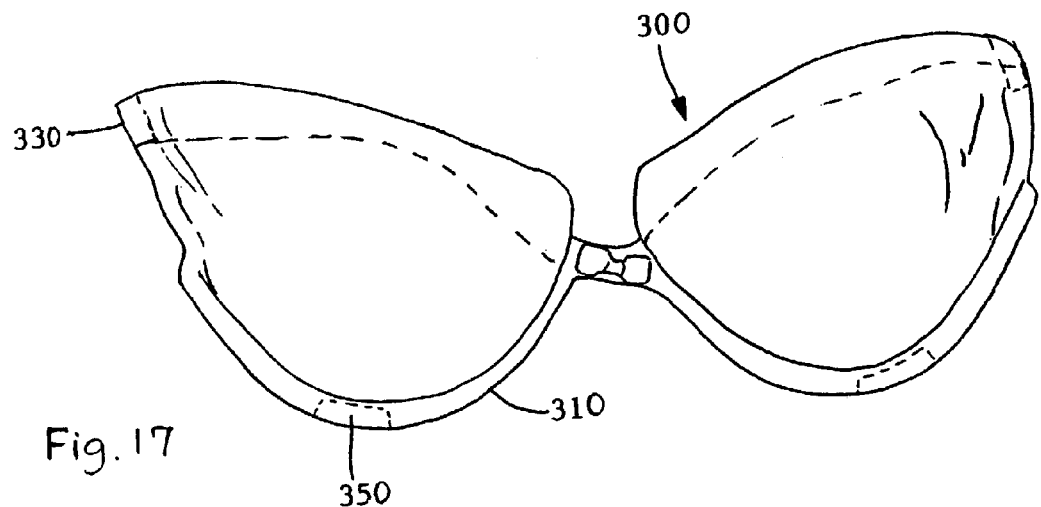
FIG. 17 illustrates an external view of the brassiere cup attachment for attaching to the posture system according to another embodiment of the present invention.
Figure 18:
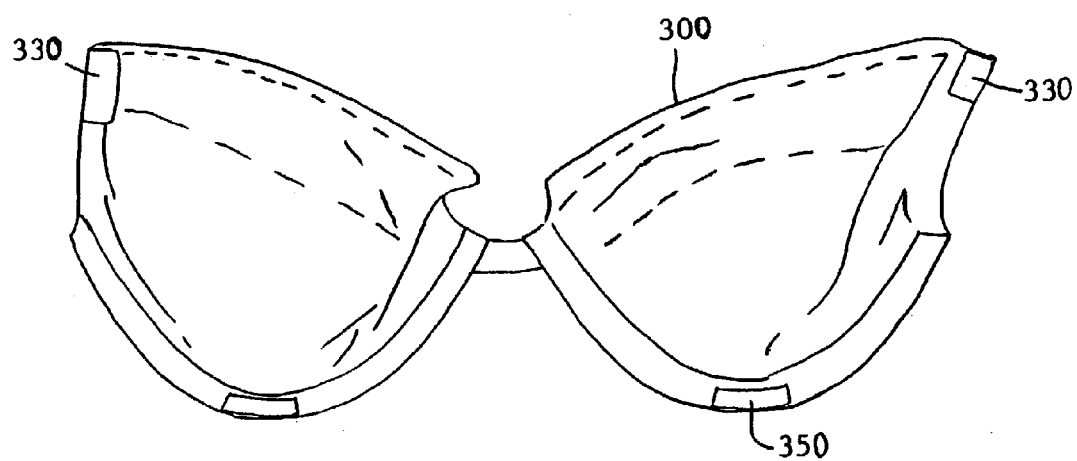
FIG. 18 illustrates an internal view of the brassiere cup attachment shown in FIG. 17.

The breast cup attachment 300 is shown in FIGS. 17 and 18, which also show the micro hook mounting patches 330 and 350. Micro hook patches 330 near the top of the breast cup attachment 300 connect to the front of the shoulder loops of the posture system, and the micro hook patches 350 connect to the frontal portion of the strap.

Figure 19:
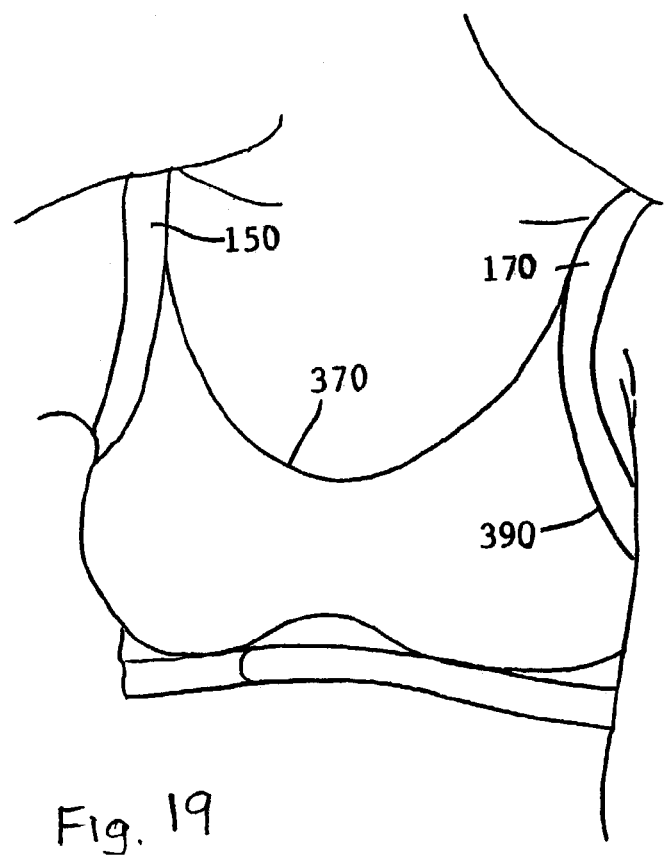
FIG. 19 illustrates a front view of the posture system according to another embodiment of the present invention with a brassiere prominently attached.

Referring to FIG. 19, a garment in which a brassiere front 370 is sewn into the shoulder-forming loops 150 and 170 all along the sides 390 of the brassiere.

Figure 20:
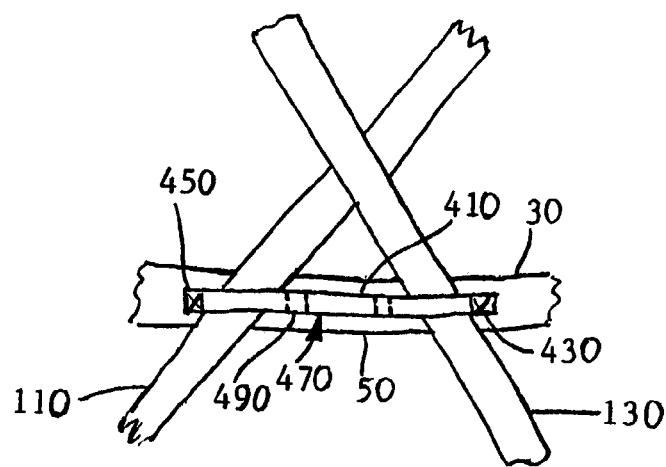
FIG. 20 illustrates an alternate view of a strap sliding attachment according to another embodiment of the present invention.

Referring to FIG. 20, illustrating an alternate form of strap end receivers, in which is a single strip of fabric 410 which is sewn at its ends 430 and 450 to the strap 30. A loop 470 results through which the ends 110 and 130 may be attached. Alternatively, the strap 410 may be two strips which are added and sewn separately to the strap 30 to provide two separate receivers for the ends 110 and 130 of the strap, or the single strip 410 may be sewn in its center in the area indicated as 490 to form two separate receivers for the ends of the straps.

Figure 21:
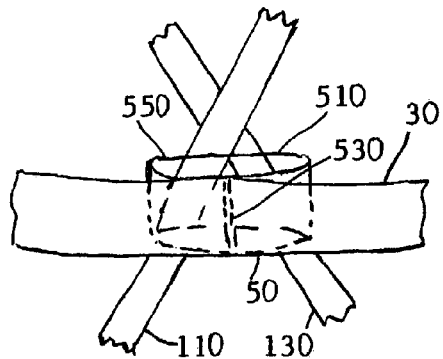
FIG. 21 illustrates an alternate receiver strap slide loop or one of two loops self-formed in the strap according another embodiment of the present invention.

An alternate form of the receivers in the central portion 50 of the strap is shown in FIG. 21. The central portion 50 of the strap is looped 510 and ends of the loop are sewn to each other and to the central portion 50 with stitches 530 to form a loop 550. Ends 110 and 130 are passed through the loop 550, which forms the receiver. Alternatively, two loops 510 may be sewn along the back portion of the strap to form separate receivers 550 for receiving the ends 110 and 130 of the strap separately.

Figure 22:
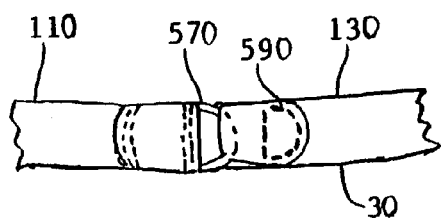
FIG. 22 illustrates an alternate D-ring attachment according to another embodiment of the present invention.

FIG. 22 shows ends 110 and 130 of the strap 30 joined by a D-ring connection 570. The D-ring is sewn into the end of strap 110, and the end of strap 130 is inserted through the D-ring and folded back upon itself where a patch 590 of micro hooks joins the micro loops which form the plush or chenille outside of the strap 30.

Figure 23:
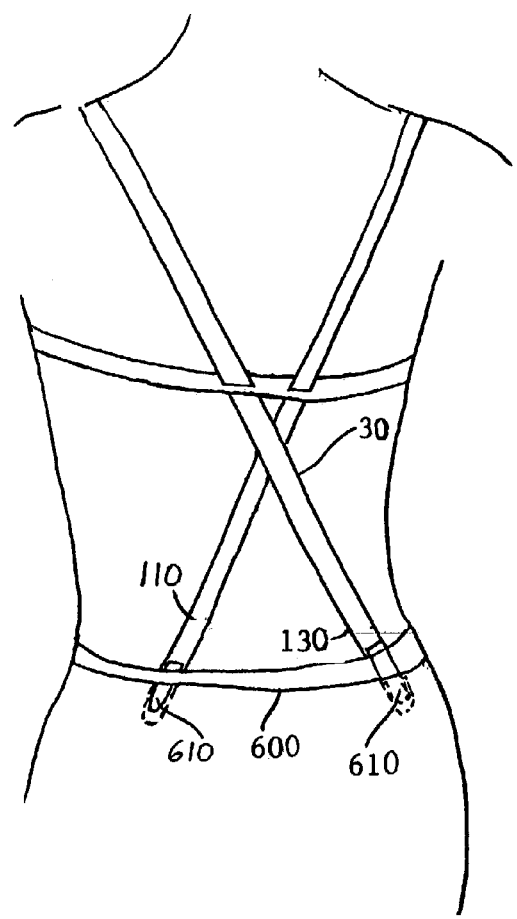
FIG. 23 illustrates attaching ends of a shoulder support strap to the rear of a belt or waistband of a garment according to another embodiment of the present invention.

Referring to FIG. 23, the ends 110 and 130 of the strap 30 are connected to a waistband 600, which may be a belt or the waistband of an undergarment. Micro hook fasteners 610 on the ends 110 and 130 of the strap 30 may cooperate with inward-facing pile fabric on the waistband 600. Alternatively, the strap may be looped around the waistband or belt, passed through openings, and joined by pressing them back against the strap end portions 110 and 130.

Figure 24:
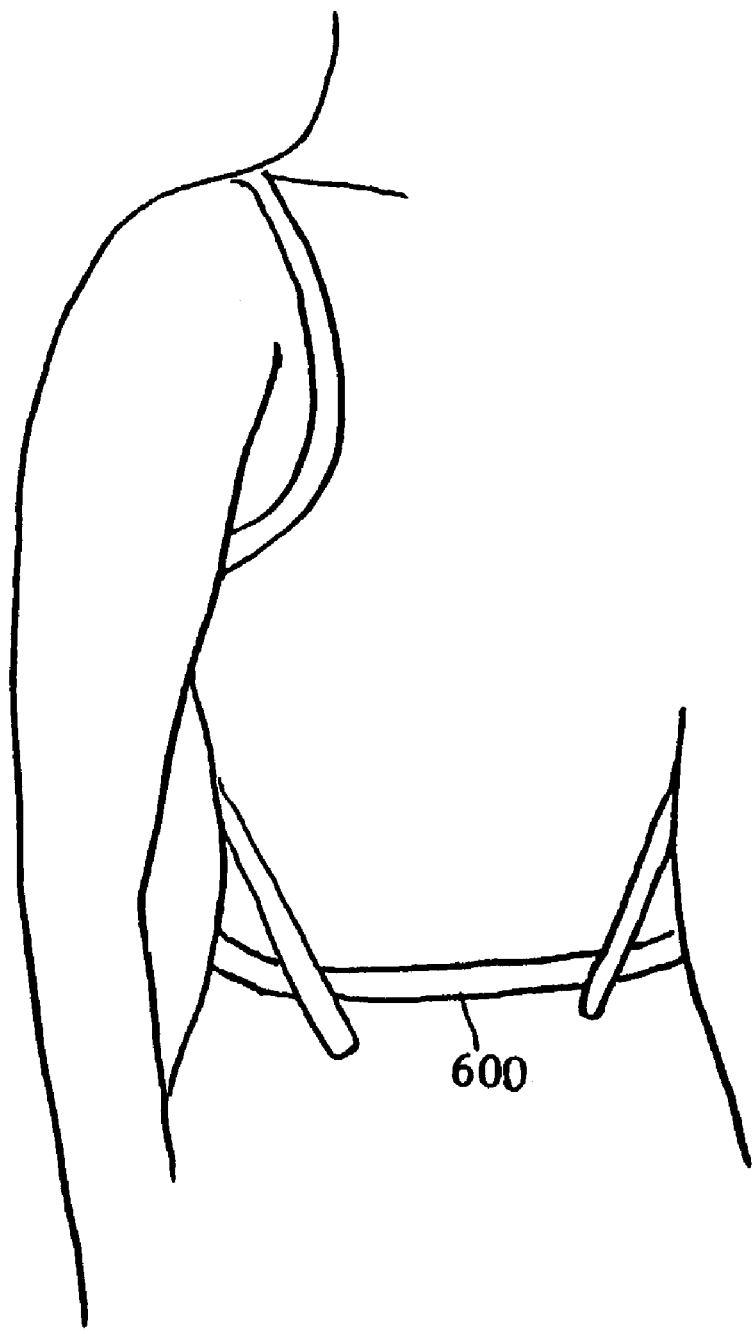
FIG. 24 illustrates attaching ends of a posture system according to an embodiment of the present invention to a front portion of a waistband or garment.

FIG. 24 illustrates a view in which the strap ends are connected to a waistband 600 at the front of the wearer's body. Alternatively, the strap ends may be connected to the waistband at the sides. The connection between the strap end and the waistband may be a series of hooks mounted on the strap and loops on the waistband, or loops and hooks mounted on the strap so that the strap may be folded upon itself around the waistband and connected to itself. Alternatively, micro fiber-type fasteners or snaps may be employed.

Figure 25:
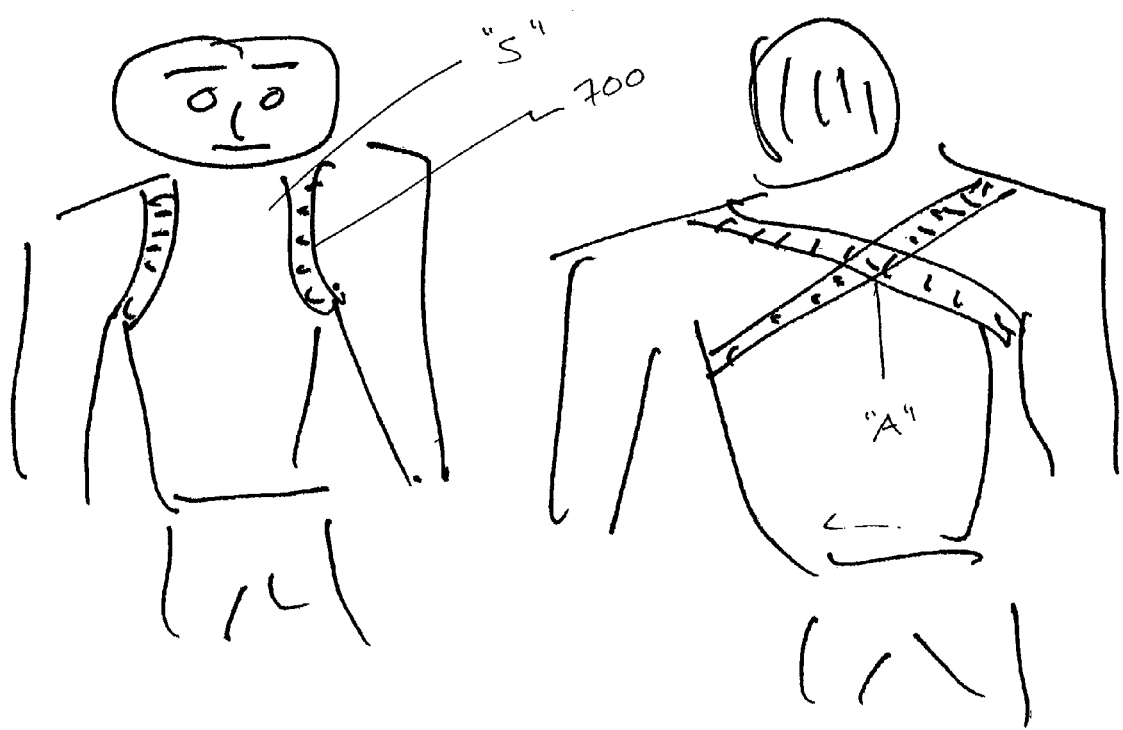
FIG. 25 illustrates a front view and rear view of the posture system according to another embodiment of the present invention.

FIG. 25 illustrates a front view and rear view of the posture system according to another embodiment of the present invention.

Referring to FIG. 25, the strap 700 may be placed about the back of the user's crossing at "A" and in front of the shoulders "S". Thereby, the strap 700 forms respective loops around the shoulders. When, the strap 700 is be crossed at substantially point "A" on the user's back as shown it is tightened. In this manner, the posture system is capable of improving a user's posture by maintaining shoulders in a posture position discouraging a forward rounding of the shoulders.

As seen from the above discussion, the present invention is directed to a posture system, which is easily and comfortably worn by a user. The posture system is of a simple design, which allows easy maintenance, care and use. That is, the present invention provides a simple, easily used, non-complex, readily adjustable and easily launderable posture system for encouraging the backward carrying of shoulders, and discouraging the forward, inward rounding of shoulders.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A posture apparatus, comprising:
 a fabric strap having central longitudinal slits and opposite ends half twisted inwardly and crossed, and passed through the slits, forming back and shoulder loops for inserting arms of a user,
 wherein the opposite ends of the strap further comprise complementary fasteners for connecting the opposite ends after tightening the strap, thereby tending to pull back shoulders of a user and straighten a user's posture.

2. The apparatus of claim 1, wherein the complementary fasteners include knotting the ends of the strap.

3. The apparatus of claim 1, wherein the complementary fasteners comprise loop formers on the opposite ends for forming a first fastening loop on one end, passing the second end through the first loop and forming a second fastening loop with a second end, thereby securing the second end.

4. The apparatus of claim 1, wherein the complementary fasteners comprise complementary micro fabric hook-type fasteners on one end for engaging fabric-type loops on a second end.

5. The apparatus of claim 1, wherein the slits comprise multiple slits for providing adjustability of a width of a user's back by selectively inserting ends of the strap through appropriate slits.

6. The apparatus of claim 1, wherein the slits are formed by a self-loop sewn in substantially a center of the strap.

7. The apparatus of claim 1, wherein the slits are formed by a separate strip sewn to a side of the strap.

8. The apparatus of claim 1, further comprising breast cups coupled to the shoulder loops at a front of a wearer's body.

9. The apparatus of claim 1, wherein opposite ends of the strap are connectable to a waistband.

10. A posture apparatus, comprising:
 a single fabric strap having a first end and a second end, wherein the strap is twisted, thereby forming shoulder loops; and
 fasteners on the first end and the second end of the strap for engaging and holding the ends after pulling on the ends and tightening the loops,
 wherein the strap includes multiple slits in strap for selectively receiving the first end and the second end of the strap and for size adjustment, and
 wherein the receivers further comprise end-tacked strips connected to central portions of the strap for receiving the first end and the second end of the strap.

11. A method for improving posture, comprising:
 arranging a first end and a second end of an elongated strap around a user's neck and under the user's arm pits and crossed around the user's back, thereby forming loops around the arms and shoulders of a user; and
 initially pulling on the first and second ends of the strap, thereby tightening the loops and pulling shoulders of the user rearward and, while continuing to pull the ends of the loops, fastening the ends of the loops in front of the user, thereby holding the loops in their tightened position while urging a user's shoulders backward.

12. The method of claim 11, wherein the initial pulling on the ends comprises pulling the ends downward and outward, and thereby tightening the loops.

13. The method of claim 11, further comprising twisting the ends of the strap half inward before passing the ends through receivers arranged on the strap.

14. The method of claim 13, wherein the fastening comprises connecting micro hooks on the first end with a strip of micro loops on the second end.

15. The method of claim 13, wherein the fastening comprises crossing the ends of the strap in front of the user's body and passing the strap ends around the loops on opposite shoulders before the ends are secured, thereby holding the loops inward on the shoulders.

* * * * *